(12) United States Patent
Cochran

(10) Patent No.: US 10,782,181 B2
(45) Date of Patent: Sep. 22, 2020

(54) RADIOGRAPH STAND WITH WEIGH SCALE

(71) Applicant: Grant Cochran, La Mesa, MD (US)

(72) Inventor: Grant Cochran, La Mesa, MD (US)

(73) Assignee: The United States of America as Represented by the secretary of the Navy, Arlington, VA (US)

( * ) Notice: Subject to any disclaimer, the term of this patent is extended or adjusted under 35 U.S.C. 154(b) by 3 days.

(21) Appl. No.: 15/946,339

(22) Filed: Apr. 5, 2018

(65) Prior Publication Data

US 2018/0328780 A1   Nov. 15, 2018

Related U.S. Application Data

(60) Provisional application No. 62/481,735, filed on Apr. 5, 2017, provisional application No. 62/633,689, filed on Feb. 22, 2018.

(51) Int. Cl.
*G01G 19/50* (2006.01)
*A61B 6/00* (2006.01)
*A61B 6/04* (2006.01)

(52) U.S. Cl.
CPC ............... *G01G 19/50* (2013.01); *A61B 6/04* (2013.01); *A61B 6/4283* (2013.01)

(58) Field of Classification Search
CPC .......... G01G 19/50; A61B 6/4283; A61B 6/04
See application file for complete search history.

(56) References Cited

U.S. PATENT DOCUMENTS

| | | | | |
|---|---|---|---|---|
| 2004/0222026 A1* | 11/2004 | Kohn | ..................... | G01G 19/44 177/25.13 |
| 2007/0287900 A1* | 12/2007 | Breen | ................... | A61B 5/4528 600/407 |
| 2010/0123083 A1* | 5/2010 | Petrick | ................. | A61B 6/4233 250/370.09 |
| 2012/0130145 A1* | 5/2012 | Sabol | ................... | A61B 6/5211 600/1 |

* cited by examiner

*Primary Examiner* — Hugh Maupin
(74) *Attorney, Agent, or Firm* — Albert M. Churilla; Ning Tang; Diane Tso

(57) ABSTRACT

A radiograph stand allowing weight placed on an injured leg/foot be measured and recorded while taking a weight-bearing radiograph. A method for taking weight bearing radiograph of a patient's foot, ankle, leg, knee, thigh, hip, pelvis, and spine.

17 Claims, 9 Drawing Sheets

RADIOGRAPH STAND WITH WEIGH SCALE

CROSS REFERENCE OF RELATED APPLICATIONS

This application claims priority to U.S. Provisional Application No. 62/481,735, filed on 5 Apr. 2017, and U.S. Provisional Application No. 62/633,689, filed on 22 Feb. 2018, which are hereby incorporated by reference.

STATEMENT OF FEDERAL SPONSORED RESEARCH

This invention was made with government support from the Defense Medical Research and Development Program (Department of the Navy). The government has certain rights in the invention.

FIELD OF INVENTION

This invention relates to a new and improved radiograph equipment, useful for obtaining weight-bearing orthopedic radiographs.

BACKGROUND

Traumatic orthopedic injuries are best evaluated with weight-bearing radiographs, such as x-rays. For example, although rotational ankle fractures contain a combination of bony and ligamentous injuries, only those injuries that are unstable require surgery. While the bony injuries are evident on x-rays, the integrity of medial ligamentous structures can be more fully evaluated using stress radiographs. Weight-bearing x-rays are one way to stress the ligaments, which can be used to determine if surgery is required (1-3). Similarly, isolated injuries to the ligaments of the syndesmosis, and the midfoot are best evaluated on weight-bearing radiographs (4, 5). In these injuries, the sprains are first graded based on imaging findings, and surgical indications are then determined.

A weight-bearing radiograph is also beneficial in the analysis and diagnosis of various orthopedic deformities. In hallux valgus, radiographic measurements including the hallux valgus angle, intermetatarsal angle, and sesamoid position are taken using weight-bearing x-rays. Physicians use these variables along with clinical symptoms to determine the appropriate treatment strategy (6, 7). Similarly, the severity of acquired adult flatfoot deformity (AAFD) can be more accurately graded using weight-bearing x-rays. Meary's line is critical in evaluation of AAFD. It measures the colinearity of the talus, midfoot, and forefoot, which is evaluated using weight-bearing x-rays (8, 9). Instability of the subtalar joint is also only detectable through weight-bearing radiography (10).

In addition to orthopedic injuries and deformities, weight-bearing radiography also benefits the diagnosis and treatment of chronic joint disease, such as arthritis. Arthritis is characterized by the loss of cartilage that normally fills the joint spaces throughout the body. Since cartilage is radiolucent, the loss of cartilage cannot be directly measured. Instead it is evaluated by measuring the space between bones while weight is applied to compress the joint surfaces together. Without reliable weight-bearing x-rays, arthritis of the foot and ankle cannot be fully evaluated (11, 12).

The functional position of the knee, hip, and spine is one of upright weight-bearing. Weight-bearing x-rays of the knee improve the evaluation of osteoarthritis (14), allow for an accurate assessment of alignment, and can provide more useful clinical information than an magnetic imaging resonance (MRI) in patients older than 40 (13). Osteoarthritis and developmental dysplasia of the hip can be more accurately staged using weight-bearing x-rays (15).

The usefulness of weight-bearing x-rays have been demonstrated across the orthopedic, sports medicine, rheumatology, and radiology literature for a number of disease processes of the lower extremities. It has been proposed as an alternative, inexpensive and superior physiologic test to guide early decision-making about for ankle stability (Hoshino et al., 2012), even over MRI. While MRI is capable of providing a lot of information, such as bone bruise patterns, osteochondral lesions, and tendon injuries, it is not ideal for acute ankle fracture diagnosis. It is both expensive and time-consuming. The clinical implications of the surplus of MRI findings can lead to unnecessary surgical procedures. In comparison, weight-bearing x-rays offer a quick, inexpensive test that is familiar to most clinicians. Many doctors are trained to interpret the x-ray without the assistance of a radiologist. Additionally, weight-bearing radiograph can directly simulate forces that a patient will be placing on the joint during the period of fracture and ligament healing.

Although useful for assessment of orthopedic injury, disease and joint deformities, a major challenge remains in taking weight-bearing radiograph, which may affect the quality of a resulting radiograph, and possibly leads to misdiagnosis. Most patients with a bone or joint problem are suffering from some level of pain, making it difficult to place their full weight onto the affected limb. For example, a patient who suffers foot or ankle injury often would slightly lift their injured foot or shift their weight to the healthy side while taking a weight-bearing radiograph in fear of further damaging the injured limb or to simply to avoid pain. Because radiograph is a record of shadows produced by objects of varying opacity to radiation on the sensitive film surface, inadequate weight placement during weight-bearing radiographs can result in images that do not accurately represent the position of the bones and ligaments. Any change in the angular position or spread position of the feet produces corresponding position changes in the bones, which distort the resulting photographs, and destroy the comparative value of the various views being taken. It is therefore extremely important that a patient remain in his/her required stance during weight-bearing x-rays so that the appropriate weight is placed on the limbs. It was revealed in one study that even healthy volunteers without pain were only able to evenly distribute their weight (within 10%) 48% of the time (16). This finding is more concerning as a clinician is routinely making medical decisions under the assumption of appropriate weight-bearing, but has no objective means of testing this. No device is currently available to allow a radiograph technician or a physician to verify the weight being born by the affected limb at the time of the x-ray. The present invention discloses an x-ray equipment that solves this problem, which comprises a stand, with a weigh scale designed for measuring the weight placed by patient while taking a weight-bearing radiograph of the foot, ankle, hip and other joints.

SUMMARY OF INVENTION

It is an objective of the present invention to provide new and improved radiographic equipment for taking weight-bearing radiographs of the lower extremity (legs, foot, knee, hip etc.) of a patient. The inventive radiographic equipment can simultaneously record the weight that is placed on the limbs by a patient during a weight-bearing x-ray. According to the presents invention, weight-bearing dorsi-plantar, medial oblique and lateral radiographs may be taken with the patient standing in his/her normal base stance, while the weight placed on the injured limb or joint is simultaneously measured and recorded.

Another objective of the present invention is to provide a new and improved method for taking a weight-bearing radiograph of a patient's foot, ankle and other joints, wherein the weight placed on the patient's limb or joint during comparative x-rays are simultaneously measured and recorded to aid later medical analysis, diagnosis and treatment. For example, a weight-bearing radiograph of an injured limb or joint may be compared to a non-weight-bearing radiograph of the same limb or joint to ensure a true stressed x-ray, which would result in a more accurate assessment of the injury.

Another objective of the present invention is to provide a new and improved radiographic apparatus, which allows comparative weight-bearing x-rays of a patient's foot, ankle and other joints be taken while recording the weights that a patient placed on different limbs/joints or while the patient is standing in different postures.

Yet another objective of the present invention is a new and improved radiographic apparatus with weigh scales that may be triggered by audio or visual cutes during a weight-bearing radiograph.

DETAILED DESCRIPTION OF DRAWINGS

DETAILED DESCRIPTION OF THE INVENTION

Figure 1:
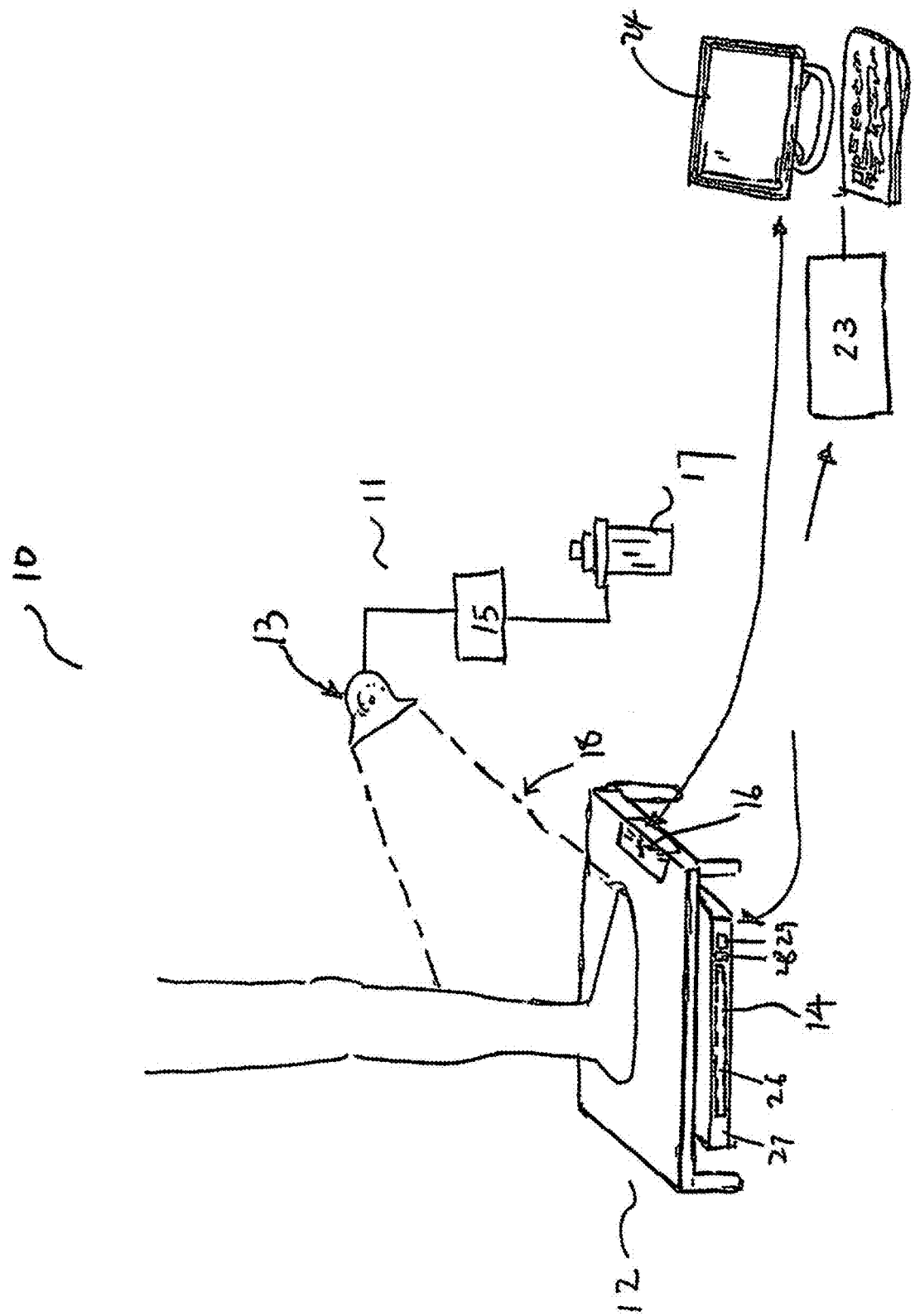
FIG. 1 is a perspective view of a weight-bearing radiography system of this invention, comprising an x-ray stand with an integrated weigh scale according to one embodiment.

It is to be noted that the term "a" or "an" entity refers to one or more of that entity. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

A radiograph is defined as an image produced on a sensitive plate or film by x-rays, gamma rays, or similar radiation, and typically used in medical examination A limb is defined a part or member of the human body distinct from the head and trunk, such as a leg, arm, or a foot.

A radiograph cassette is defined as an image receptor, which includes but is not limited to a container used to hold radiographic film, storage phosphor plate, a charge coupled device, thin-film transistors, photoconductor, or x-ray scintillator.

The above and other objects and advantages of the present invention will be more apparent from the following detailed description of the preferred embodiments when read in connection with the accompanied drawings, where in like reference numerals designate like or corresponding parts throughout the figures:

As shown in FIG. 1, a radiograph system 10 according this invention comprises of an x-ray radiator 11 operatively connected to a radiographic equipment 12. The x-ray radiator 11 further comprises of an x-ray source 13, an x-ray source controller 15 and an activator switch 17. An x-ray source 13 typically has an x-ray tube for radiating x-rays, and a collimator for limiting the irradiation field of x-rays 18 from the x-ray tube. The radiographic equipment 12 according to this invention may comprises an electronic cassette 14 for capturing radiography, an image acquisition controller 23, a weigh scale 16 and a console 24. The electronic cassette 14 mainly comprises of a flat panel detector (FPD) 26, which functions as a radiographic image detector and a housing 27 that contains the FPD 26. The electronic cassette 14 is a portable x-ray image detector that receives x-rays from the x-ray source 13 after they penetrating through a limb or joint of a patient 19, thus producing an x-ray image (radiograph) of that limb or joint 19. The electronic cassette 14 is provided with a communicator 29 for communication with the console 24, and a memory 28 for storing a cassette ID. The cassette ID 20 is information necessary for the console 24 to identify each individual cassette 14 among many cassettes communicably connected to the console 24. An example of the console is a computer or a device equipped with a microprocessor. The cassette ID 20 is attached to communication data that is exchanged between the console 24 and each cassette 14 so the communication data can be linked to the patient who is taking the x-ray. This data communication may be accomplished via wire or wireless communication.

Figure 2:
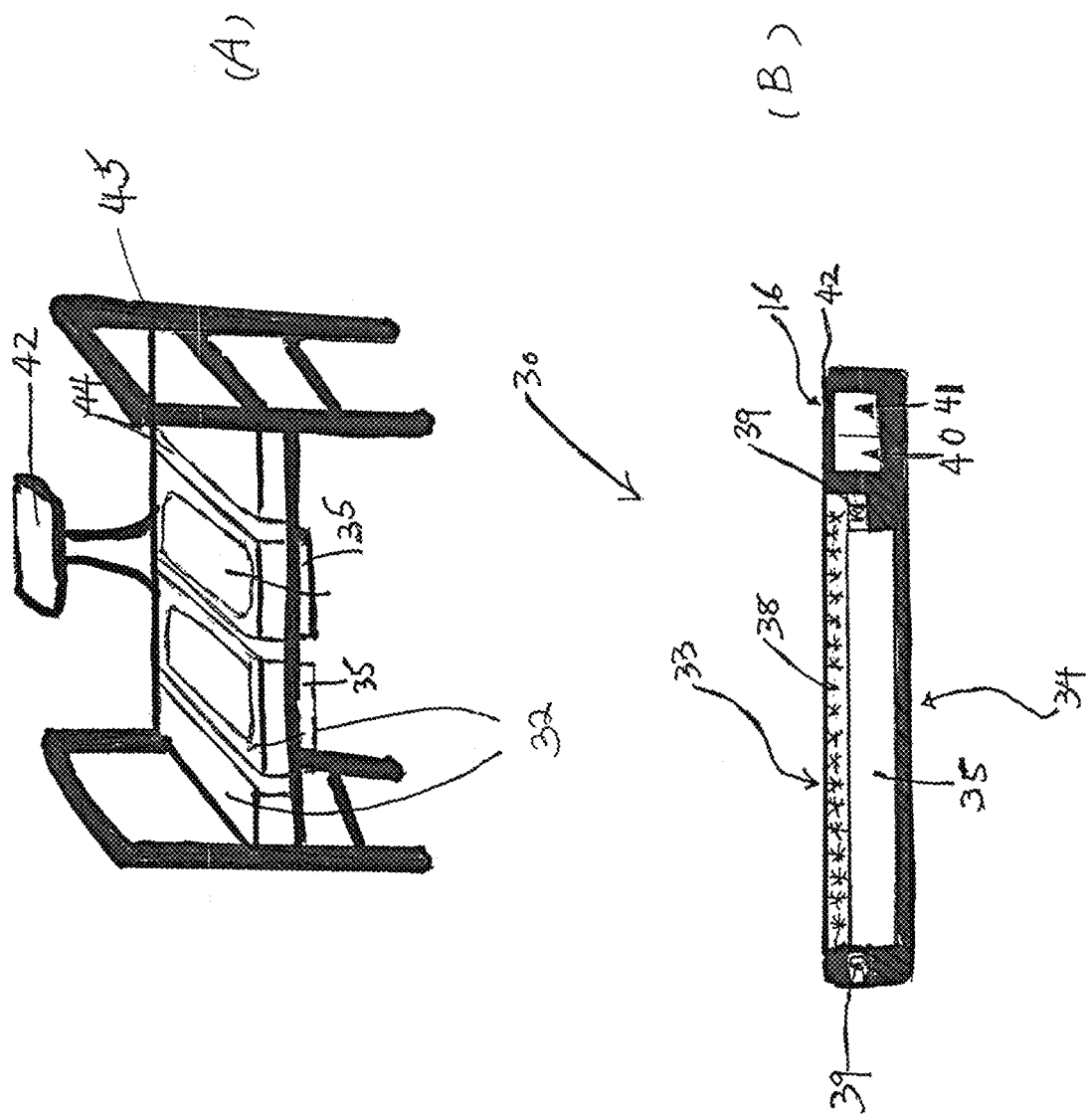
FIG. 2 is a perspective view of an embodiment of the presented invention, which is x-ray stand with integrated weigh scales (A) and its cross-sectional view (B).
Figure 3:
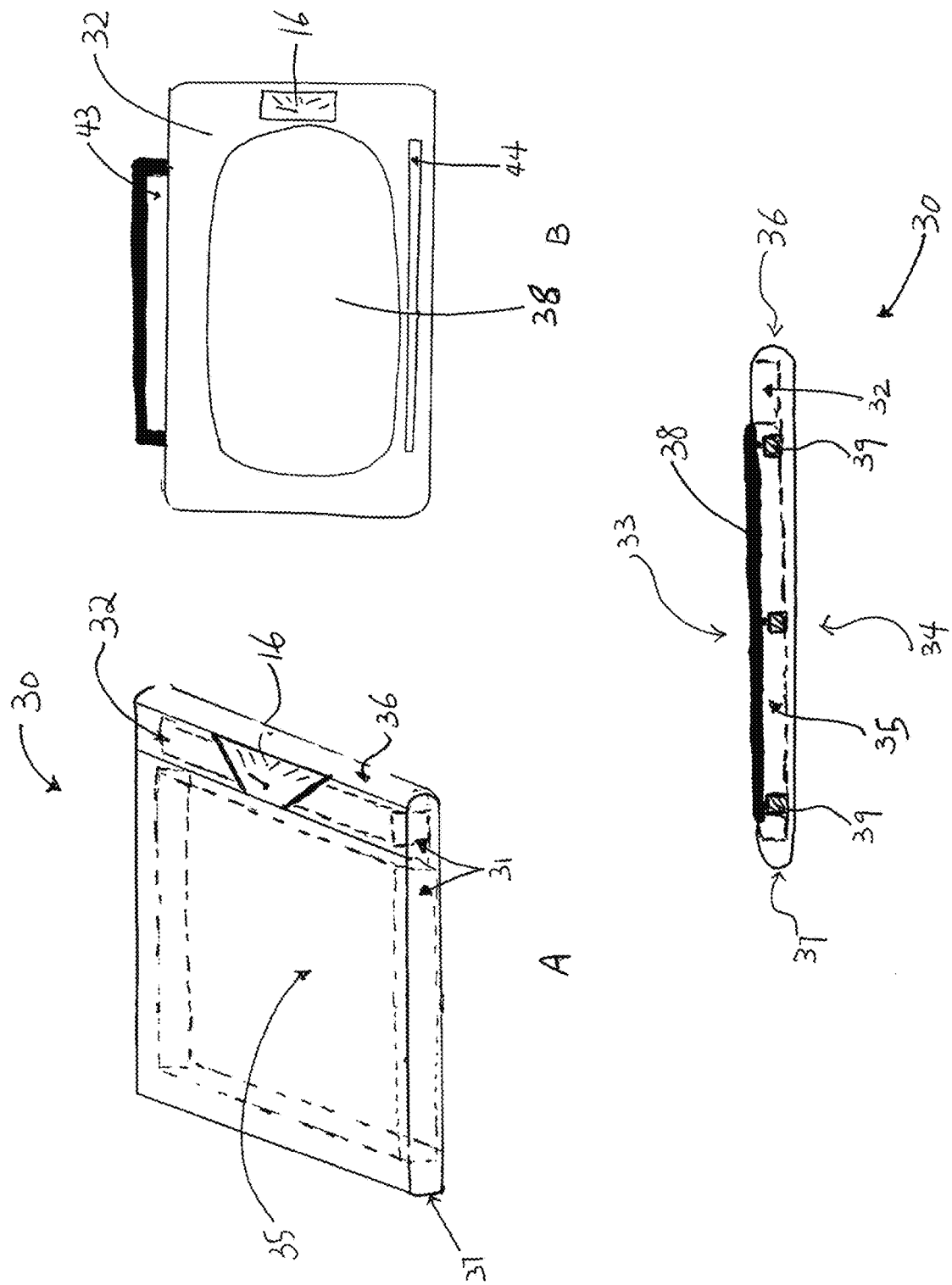
FIG. 3 shows a perspective view of an embodiment of the present invention, wherein the weight-bearing x-ray stand is a cassette protector with an integrated weigh scale (A) a top view (B) and a cross-sectional view (C) of the same embodiment.
Figure 4:
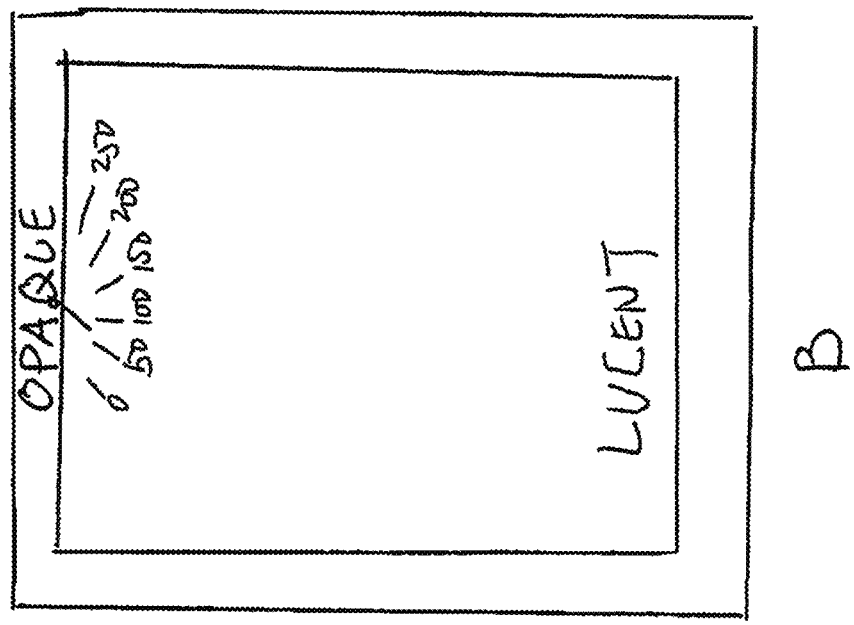
FIG. 4 shows the top view of an embodiment of the present invention, wherein the x-ray stand has double weigh scales with mechanical display (A) and a top view of the same embodiment (B).
Figure 4:
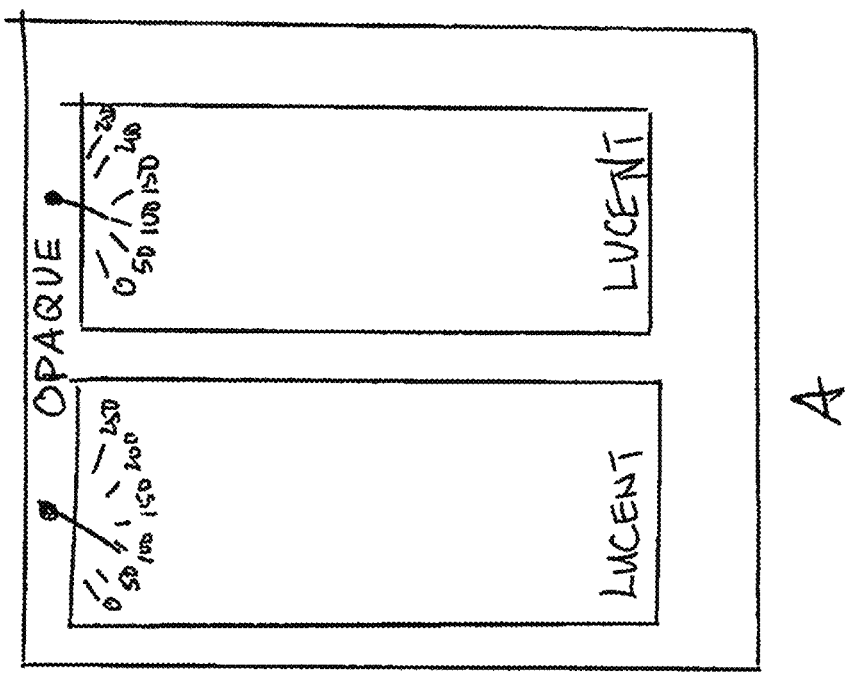
Figure 9:
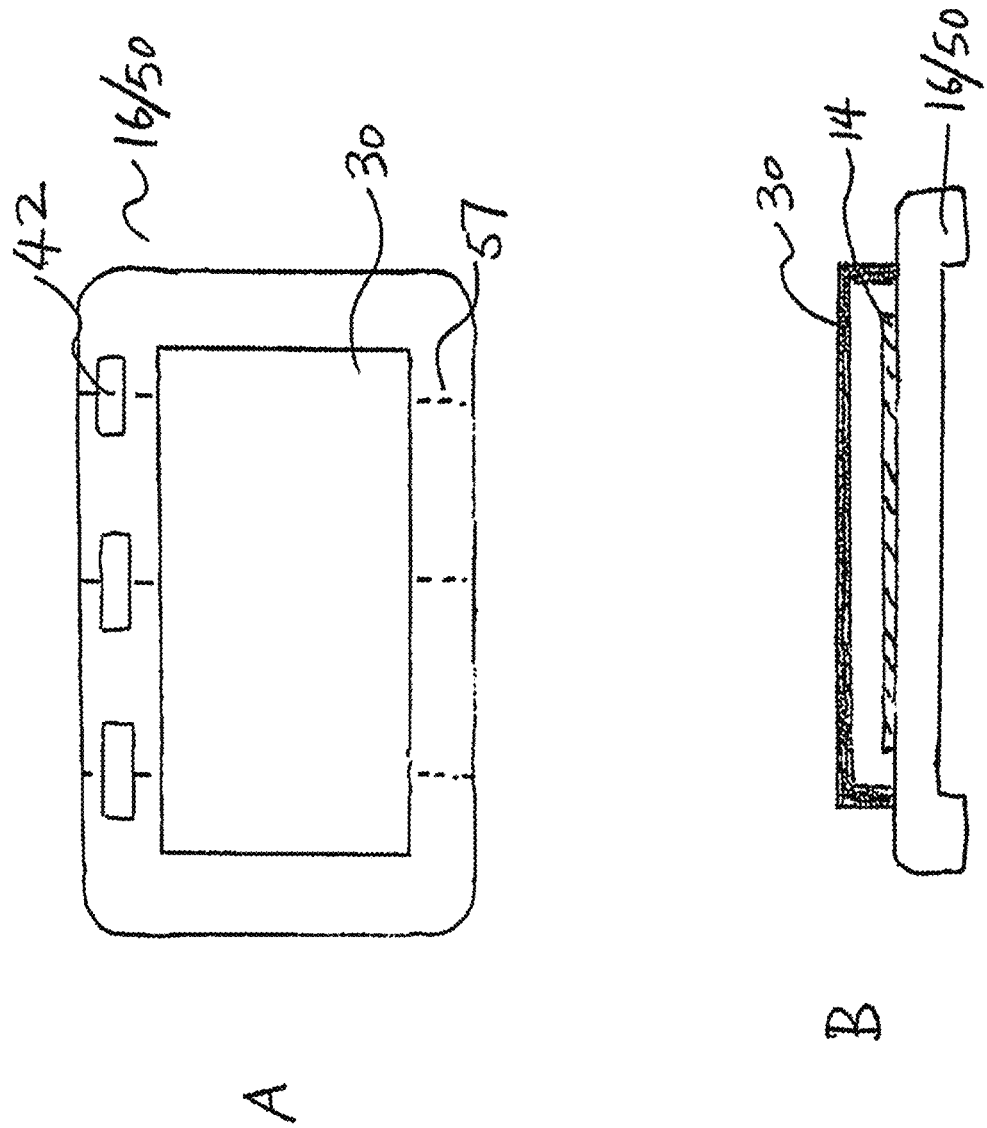
FIG. 9 shows a top view of an embodiment of the inventive device being used in taking AP and oblique x-rays of the foot while placed under the x-ray cassette and cassette protector (A) and a side of view of an embodiment of the inventive device being used in taking AP and oblique x-rays of the foot while placed under the x-ray cassette and cassette protector.

In the present invention, one or more weigh scale 16 may be incorporated into a radiograph stand as shown in FIG. 2A-B, or incorporated into a radiograph cassette protector as shown in FIG. 3A-C or acting as a stand-alone unit capable of measuring weight measurements while taking weight-bearing radiograph, as shown in FIG. 9. Using the weigh scale of the present invention, weight a patient placed on one or both legs/foots/joints during a weight-bearing x-ray can be measured and recorded. The weight measurements can be either displayed directly on the weighing apparatus, such as on display screen of the weigh scale as in FIG. 4, or be separately measured, recorded, communicated and displayed by a console as shown in FIG. 1. The weight measuring mechanism of the weigh scale 16 can be either electronic or mechanical. They are housed in the radiopaque part of the radiograph cassette protector or radiograph stand. Such electronic and mechanical weight measuring mechanism are well-known in the art, and can be easily adapted for the present invention. Some examples are described in U.S. Pat. Nos. 4,219,092, 6,700,080, 4,336,3368, etc.

The weigh scale 16 may further comprises a triggering mechanism, which is communicatively connected to the activator switch 17, the image acquisition controller 23, and/or the console 24. Examples of a triggering mechanism are described in U.S. Pat. No. 4,387,722, or U.S. Pat. No. 5,887,049, which can be easily adapted for this invention. When triggering mechanisms are activated, the weight a patient placed on selected weigh scales are measured, while x-rays of the patient's leg/foot/joint are simultaneously taken. The triggering mechanism may also comprises an audio or visual sensor, which triggers the radiographic system of the present invention to take the weight measurements and x-ray simultaneously in response to an auditory or visual cue. For example, an audio trigger may be a sound generated by an x-ray machine or the technician. Commercial x-ray machines are normally equipped with a safety buzzer that is sounded when the x-ray tube is active and emitting radiation. This buzzer sound can be detected by an audio sensor and programmed to trigger the weigh scale/x-ray so that weight measurements are taken and recorded when an x-ray is taken. There are several types of audio activated triggering mechanisms known in the art, which may be adapted for this invention. An example of a simple audio-actuated switch is described in U.S. Pat. No. 3,582,671. The audio-actuated switch of Patent '671 includes a thyristor, preferably an SCR, the gate of which is triggered by an audio frequency signal from a microphone and audio amplifier. The amplifier is a class A audio amplifier with biasing and loading provided so that a light will be activated by sound above a selected level. A nonlinear potentiometer is used for the load impedance of one of the amplifier stages to permit selection of the desired audio level which triggers the thyristor. The input terminals of a rectified power supply are connected across the principal terminals of the SCR so that the parallel combination may be connected in series with the electric light and an alternating current power source. A signal process circuit may also be connected a microphone and used to identify the frequency and intensity of a pre-programmed sound signal. A speech activated triggering mechanism may also be used in the present invention. One of such triggering system is described in US20090138507, which employs speech emanating from the user as the triggering event.

The weight scale of the present invention may also be triggered by a pre-programmed weight ratio between selected weigh scales. For example, during a comparative weight-bearing x-ray, when weights placed a patient on different weigh scale reaches a target ratio, the triggering mechanism 47 sends signals to the activator switch 17, the image acquisition controller 23 and/or the console 24, allowing the weights placed on the different weigh scales during a comparative weight-bearing radiograph be simultaneously measured and recorded. This ensures that a true stressed x-ray of the patient's injured leg/foot/joint.

An embodiment of a radiograph stand of the present invention is shown in FIGS. 2A and 2B, wherein weigh scales are incorporated into the radiograph stand platform. FIG. 2A shows a weight bearing x-ray platform 45, with one or more receptor slot or holder 44 on top of the platform allowing vertical placement of electronic cassette 14 for taking lateral radiograph of the foot and ankle. One or more cavities 35 are provided under the platform 45 for insertion of an electronic cassette 14 when taking dorsi-plantar, medial oblique radiograph of the foot and ankle. Each electronic cassette cavities 35 is covered by a radiolucent plate 38 with the plane size slightly larger than the surface of radiographic cassette 14. The radiolucent plate 38 is operatively connected to one or more weight sensors 39 (FIG. 2B), allowing weight of placed on the radiolucent plate 38 to be measured, recorded, and shown on a display 42, and/or communicated to a console 24. Alternatively, the platform contains no cassette cavities, but is partially covered by a radiolucent plate 38 with the plane size slightly larger than the surface of radiographic cassette 14, which is operatively connected to one or more weight sensors 39 housed in radiopaque region 32 of the platform. A radiographic cassette 14 is directly placed on the floor underneath the radiolucent plate 38, while the weight-bearing x-ray is taken. The weight of placed on the radiolucent plate 38 is then measured, recorded, shown on a weight display 42 and/or communicated to a console 24. The weight bearing x-ray platform 45 may also include a handle 46 for the patient to hold on to so the patient can stand as close to their normal stance as possible without losing balance. The radiopaque region 32 (FIG. 2A and FIG. 2B), which may be the frame enclosing the radiolucent region, houses the mechanical and/or electronic components of the weigh scale 16, such as weight display 42, weight sensors 39, memory 40 and communicator 41.

In FIG. 3A-C, a different embodiment of the weight-bearing radiograph stand of the present invention is shown as a radiograph cassette protector 30. The radiograph cassette protector 30 has a flat planner body having substantially rectangular top surface 33 and bottom surface 34, and at least two opposing side panels 36 or 37, forming an interior cavity 31. The interior cavity 31 is separated into a radiolucent region 35, and a radiopaque region 32. The radiolucent region 35 has a plane size slightly larger than the size of a radiographic cassette 14, and creating a cavity adapted for the insertion of a radiographic cassette 14. The radiopaque region 32, which may be the frame that is encasing the radiolucent region 35, houses the mechanical and/or electronic components of the weigh scale 16, such as weight display 42, weight sensors 39, memory 40 and communicator 41.

As shown in FIG. 3C, the radiolucent region 35 is covered with a radiolucent plate 38, which is operatively connected with the weigh sensors 39 housed in the radiopaque frame 32 of the weight-bearing radiograph cassette protector 30. The other electronic/mechanical component of the weigh scale 16, may include weight display 42, memory 40 and communicator 41. As shown in FIG. 3B, the weight-bearing radiograph cassette protector 30 of FIG. 2A, may further comprise one or more receptor slot 44 or holder 43 on top or on the side, allowing vertical placement of electronic cassette 14 for taking lateral radiograph of the foot and ankle.

FIG. 4A-B shows the top view of the platform surface of a weight-bearing x-ray stand of the present invention. FIG. 4A illustrates a weight-bearing x-ray stand with double weigh scales, which are capable of measuring weights a patient placed on both leg/foot/knee during a weight-bearing x-ray. Each weigh scale may further contain locking mechanisms that can disable the operation of a weigh scale when only the weight of one foot is needed. FIG. 4B shows an alternative embodiment of FIG. 4A, which contains only a single weigh scale. In both embodiments, the weigh scale may be electronic or mechanical. Alternatively, the weight-bearing x-ray stand of the present invention may also include up to four weigh scales, allowing comparative weight-bearing x-rays be taken between different leg/foot/joint or at different postures.

Figure 5:
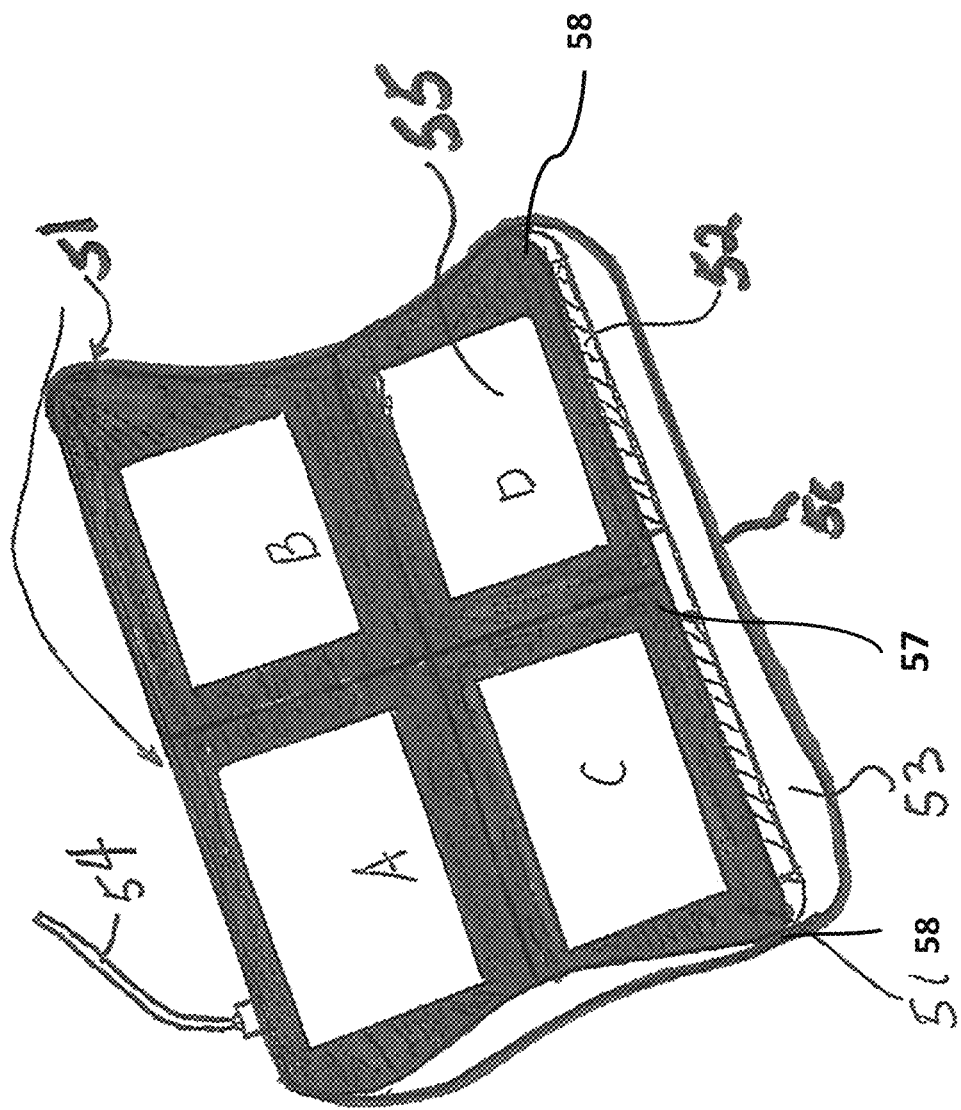
FIG. 5 shows another embodiment of the present invention, wherein x-ray stand is a balance board with four weigh areas.

FIG. 5A shows yet another embodiment of the present invention, comprising a weigh scale board 50 similar to a Wii Fit balance Board. A weight scale board 50 for taking weight-bearing x-ray of the foot, leg, knee or other joint, comprising: a base unit 53, said base unit configured in size and shape to securely and stably hold one or more weight sensing platform 51A-D; at least one anchor point 58 disposed on said base in a vicinity of a terminal end of said weight sensing platform 51A-D; and a resistance mechanism 57 attached at a first end by a fastener (not shown) to said anchor point such that when a user positioned on said balance and weight sensing platform 51A-D exerts a force on a holding loop (not shown) attached to a second end of said resistance mechanism 57 said balance and weight sensing platform senses said exerted force and said balance and weight sensing platform senses an apparent shift in a center of balance occasioned by said exerted force. The weigh sensing platform 51A-D may further comprising a radiolucent plate 55 and a radiopaque housing 56. An x-ray cassette receptor 52 may be provided directly below each radiolucent plate 55 sized and adapted to receive an x-ray cassette. The weight resistance mechanism, the fasteners and the anchor point are all provided within said radiopaque housing.

The weigh scale board 50 contains up to four weight sensing platform areas 51A-D. Each weight sensing platform areas area 51A-D can be used as an individual weigh scale or used in combination. The weigh scale board 50 is communicatively connected to a weight sensing platform area selector (not shown), which is communicatively connected to the triggering mechanism 47 and/or the console 24. The communication may be conducted by wire 54 or wireless connections. Weight sensing platform area selector allows the technician to select the weight sensing platform areas 51A-D to be used in an x-ray, and communicate that selection to the console. The weight a patient placed on the selected weight sensing platform areas 51 during a weight-bearing x-ray are then measured and recorded. A weigh measuring mechanism 56 is housed underneath weight sensing platform areas within the radiopaque housing 56. The weigh measuring mechanism may be electrical or mechanical and are both well taught in the art. An example of a weigh measuring mechanism that can be used for this embodiment, is described in US20110218077 (Juan Fernandez), and is hereby incorporated in this invention. An alternative weigh measuring mechanism may be plurality strain gauge sensors and software similar to which used in a Wii balance board (as described in Appendix A and hereby incorporated by reference). It is understood that many other weigh measuring mechanisms may be used in the weigh scale board of this invention, and is not limited to the examples, figures and descriptions of this application.

Comparative x-rays of different leg/foot/joint may be taken simultaneously while the patient places each foot in a different weight sensing platform areas 51. The triggering mechanism 47 may trigger the activator switch 17 when a target weight ratio is reached between the selected weight sensing platform areas. X-rays of limbs positioned on those selected weight sensing platform areas are automatically activated and taken. In an alternative embodiment, the weights that a patient placed on the selected weight sensing platform areas 51 are measured when the weigh measuring mechanism is activated by a buzzer sound of an x-ray machine or the voice of a technician. Weight scale board may also comprises a light sensor. When x-ray is activated, the light sensor triggers the weight scales, and allow weight measurements placed selected weight sensing platform areas 51A-D to be taken and recorded. The total weight placed on all selected weigh area may be also measured and recorded.

In yet another embodiment as shown in FIGS. 9 A and B, the weigh scale 16 or weigh scale board 50 may be used as a stand-alone unit. The top surface of the weigh scale 16/weigh scale board 50, comprises three separate weight sensing platform areas 51, which is marked with lines 57 to aid the technician to properly position the patient's feet on the scale. The weigh scale 16/weigh scale board 50 may further comprises one or more weight displays 42, which provide readout of the weight placed on the left foot (left display), the right foot (right display) and/or the total weight (center display). In situation where the weigh scale 16 is in the direct path of the x-ray beam, such as for AP and oblique views of the foot, the radiograph cassette 14 and cassette protector 30 is placed on top of the stand-alone weigh scale 16/weigh scale board 50.

Example 1: Operation of the Weight-Bearing X-Ray Stand in Taking Radiograph of the Patient's Foot or Ankle To use the inventive x-ray stand to take a lateral radiograph of the patient's foot or ankle:
  a) Let the patient stand in his or her normal base stance with the foot firmly positioned on the x-ray stand platform or the cassette protector;
  b) Make sure the foot that is being x-rayed is planted on a radiolucent plate of the weigh scale with the lower leg perpendicular to the floor or weight-bearing X-ray stand surface;
  c) An electronic cassette is then placed in slot or a vertical x-ray film holder, next to the injured feet which allows a radiograph cassette to be held parallel to the patient's foot axis for lateral x-ray to be taken;
  d) The central beam is directed through the foot perpendicular to the axis of the foot, and the detector;
  e) The x-ray and the weigh scale is activated;
  f) The weight placed on the injured foot during x-ray is measured and recorded; and
  g) A non-weight bearing x-ray of the injured feet or an X-ray of the patient's healthy foot may be taken with weight placed on each foot recorded for comparison.

To use the inventive x-ray stand to take a weight-bearing dorsoplantar foot/ankle radiograph of the patient's foot or ankle:
  a) Let the patient stand in his or her normal base stance with the foot firmly positioned on the x-ray stand platform or the cassette protector;
  b) Make sure the foot being X-rayed is planted on the cassette protector or platform's radiolucent plate with the lower leg perpendicular to the floor or weight-bearing surface;
  c) A radiographic cassette is inserted in the cassette cavity;

d) The central beam is angled approximately 15 degrees towards the heel to minimize projecting the tibia and fibula over the hind foot;
e) The x-ray and the weigh scale is activated;
f) The weight-bearing, non-weight-bearing radiographs of the injured foot and radiograph of the healthy foot during normal stance may then be taken for later comparison; and
g) Weight placed on each foot during radiograph is measured, recorded, displayed and or communicated to the console.

Example 2: Operation of the Weight-Bearing X-Ray Stand in Taking Radiograph of the Patient's Knee The knee is a weight bearing joint and therefore for all intents and purposes, knee x-rays should be taken while weight bearing. As radiographs are a two-dimensional representation of a three-dimensional bony structure, radiographs of the knee are normally taken in two planes at right angles to each other to infer all three dimensions. For example, a radiograph may show a complete loss of medial (inner) joint space, which was not evident on the standing anteroposterior (AP, front-back) x-ray. The 45° flexed PA standing view of the knee is a much more sensitive x-ray in showing early degenerative disease in the position of function. For example, the 45° flexed PA standing view of the knee provides an accurate definition of the width of the intercondylar notch, which is very useful information for patients undergoing ACL reconstruction. The standing AP x-ray will give an indication of the presence of degenerative disease within the knee. Standing AP is also an indication of the alignment of the knee joint. The width of the intercondylar notch gives indication of the size of the contents of the notch, which are the anterior and posterior cruciate ligaments. 60% of the notch is occupied by the PCL, 40% by the ACL approximately. The patients with a narrow notch are more likely to tear their ACL's as this is an indication of a small anterior cruciate ligament. Measuring the size of the notch on the x-ray allows the surgeon to plan the degree of notchplasty that is required. In certain situations, it can also help the surgeon to decide whether to use an ipsilateral or contralateral patella tendon graft for the ACL reconstruction. As people do not walk with their knees fully extended, but tend to have their knees flexed during the gait cycle, a flexed x-ray view brings the weight bearing part of the knee joint into the view on the radiograph. All these views will also show fractures about the knee and may give information to direct further imaging studies.

Figure 6:
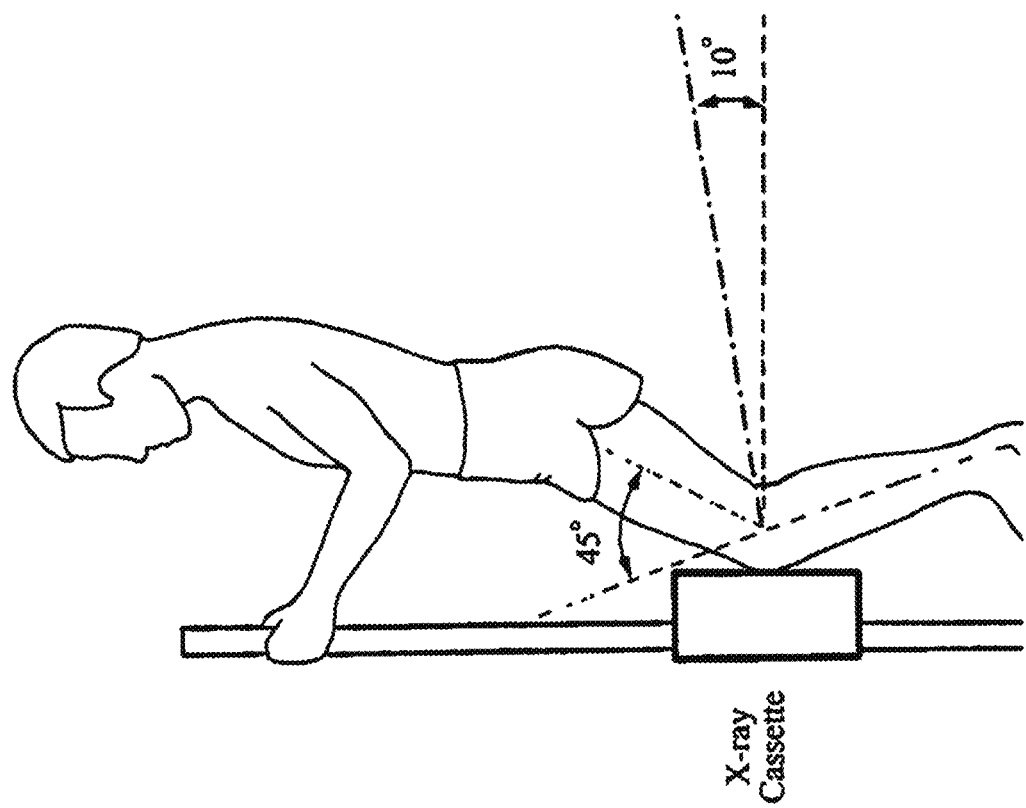
FIG. 6 illustrates how comparative weight-bearing x-rays of both knees may be simultaneously taken.

FIG. 6 shows how a knee AP weight-bearing view is taken using a weigh scale board of this invention:
a) The patient is erect on a weigh scale board or stand of this invention against the upright detector with each foot standing in two weigh scale areas (FIG. 5 51AB or FIG. 5 51CD);
b) make sure that patient's knee is flexed at approximately 45° with grid in front of knees;
c) ensure patient's knee is not rotated;
d) direct beam approximately 10° caudal from the horizontal plane through the knee joint
e) activate the x-ray either manually, via audio and/or visual signal or automatically when a preset target weight ratio between the two weigh scale areas is achieved
f) weight placed on each foot during radiograph is measured, recorded, displayed and or communicated to the console
g) Each x-ray is associated with the cassette ID and weight measured.

Figure 7:
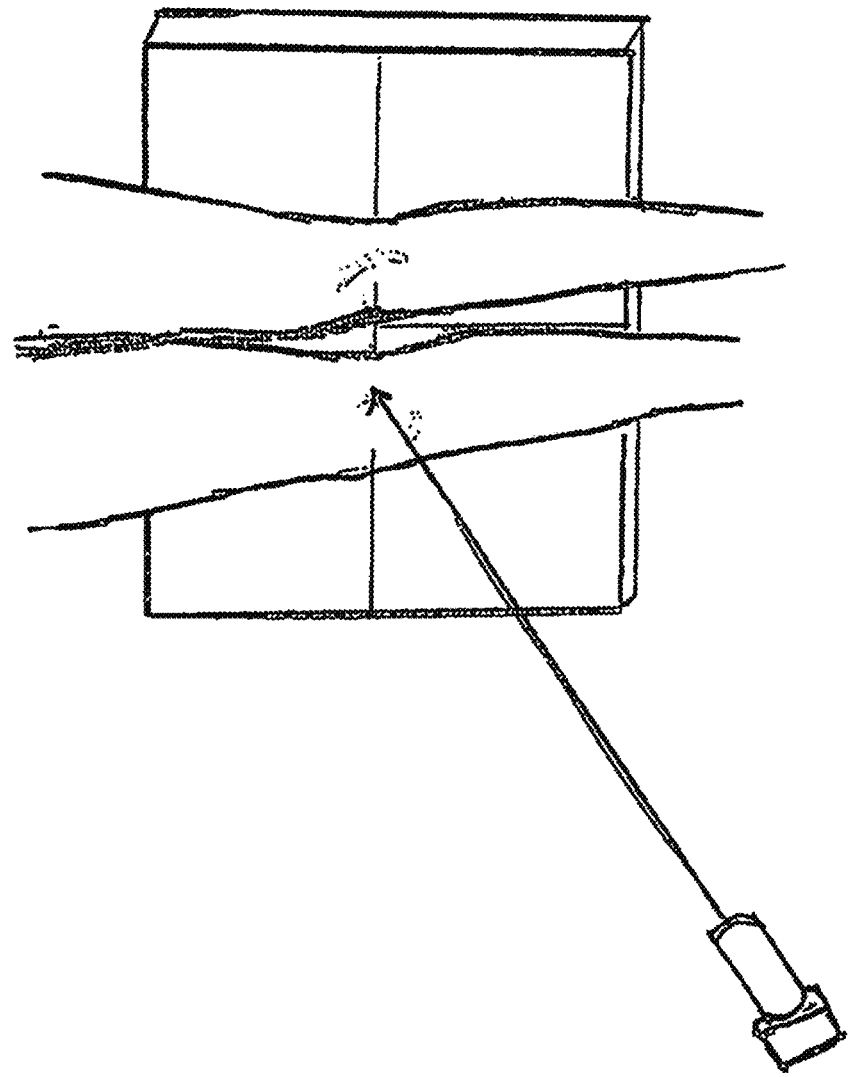
FIG. 7 shows how to take weight-bearing AP view of a patient's knee using a weigh scale board of this invention.
Figure 8:
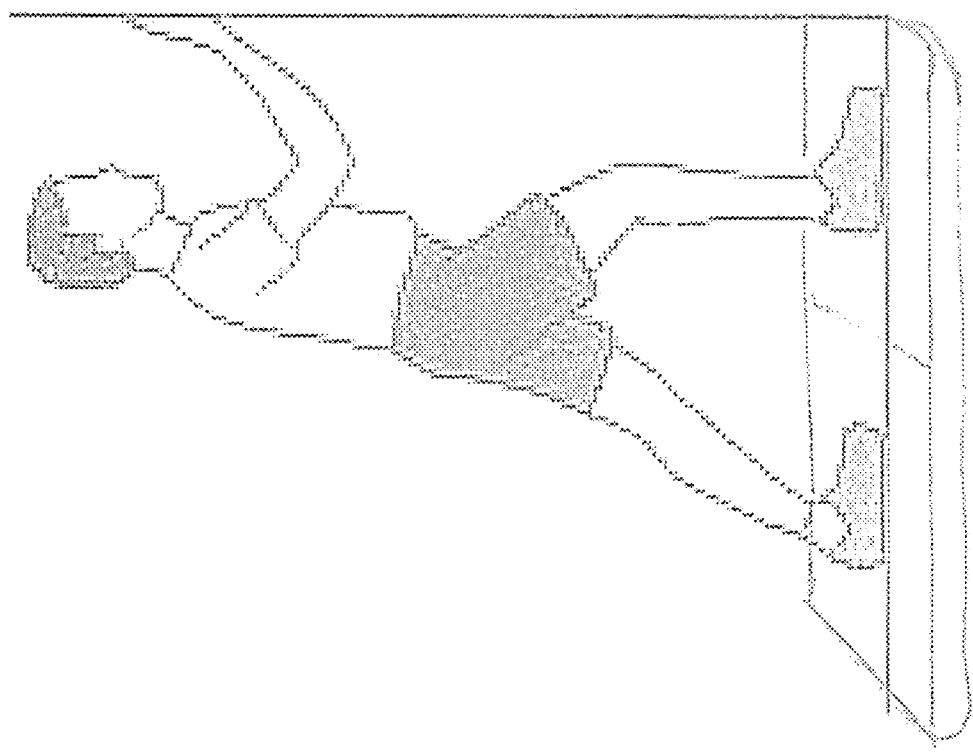
FIG. 8 shows how to take weight-bearing x-ray of patient knee can be taken while the patient takes a forward lunge.

FIG. 7 shows how to take weight bearing AP view of a patient's knee using a weigh scale board of this invention:
a) The patient is erect on a weigh scale board in upright position with back toward vertical grid device on the upright detector with each foot standing in two weigh scale areas
b) Make sure the patient's toes straight ahead, with feet separated enough for good balance.
c) Ask patient to stand straight with knees fully extended and weight equally distributed on feet.
d) Place central ray Horizontal and perpendicular to center of IR, entering at point 1.3 cm below apices of patellae.
e) activate the x-ray either manually, via audio and/or visual signal or automatically when a preset target weight ratio between the two weigh scale areas is achieved
f) weight placed on each foot during radiograph is measured, recorded, displayed and or communicated to the console
g) each x-ray is associated with the cassette ID, weight measured Example 3: Operation of the Weight-Bearing X-Ray Stand in Taking Radiograph of the Patient's Knee in Different Position FIG. 8 shows how to take weight-bearing X-ray of patient knee can be taken when the patient takes a slight forward lunge
a) The patient is stand on a weigh scale board face toward vertical grid device on the upright detector
b) Asking the patient to take a step forward into a slight lunge, so the patient's two feet are standing in two different weigh scale area
c) Make sure the patient's toes straight ahead, with feet separated enough for good balance, and weight equally distributed on feet.
d) Place central ray parallel to the joint surface of the tibial plateau
e) activate the x-ray either manually, via audio and/or visual signal or automatically when a preset target weight ratio between the two weigh scale areas is achieved
f) weight placed on each foot during radiograph is measured, recorded, displayed and or communicated to the console
g) each x-ray is associated with the cassette ID and weight measured

REFERENCES

1. Stewart C, Saleem O, Mukherjee D P, Suk M, Marymont J, Anissian L.Foot Ankle Int. 2012 July; 33(7):548-52. Axial load weightbearing radiography in determining lateral malleolus fracture stability: a cadaveric study.
2. Hastie G R, Akhtar S, Butt U, Baumann A, Barrie J L. J Foot Ankle Surg. 2015 November-December; 54(6): 1042-6. Weightbearing Radiographs Facilitate Functional Treatment of Ankle Fractures of Uncertain Stability.
3. A Novel Algorithm for Isolated Weber B Ankle Fractures: A Retrospective Review of 51 Nonsurgically Treated Patients. Holmes JR1, Acker W B 2nd, Murphy J M, McKinney A, Kadakia A R, Irwin T A.
4—Foot Ankle Int. 2015 October; 36(10):1202-8. doi: 10.1177/1071100715588186. Epub 2015 Jun. 3. The Fate of the Fixed Syndesmosis Over Time. Gennis E1, Koenig S2, Rodericks D3, Otlans P3, Tornetta P 3rd4.
5—Classification, Investigation, and Management of Midfoot Sprains Lisfranc Injuries in the Athlete James A. Nunley,* M D, and Christopher J. Vertullo, MBBS, FRACS American Journal of Sports Medicine 2002
6—Measuring sesamoid position in hallux valgus: when is the Foot Ankle Int. 2011 August; 32(8):782-8. Radiographic considerations of hallux valgus versus hallux rigidus.
7—Foot Ankle Int. 2015 April; 36(4):391-4. doi: 10.1177/1071100714560400. Epub 2014 Dec. 3. Radiographic results after hallux metatarsophalangeal jointarthrodesis for hallux varus. Geaney LEI, Myerson MS2.
8—Orthop Traumatol Surg Res. 2015 February; 101(1 Suppl):S11-7. doi: 10.1016/j.otsr.2014.07.030. Epub 2015 Jan. 13. Adult flatfoot. Toullec E1.
9—J Bone Joint Surg Am. 2014 Apr. 16; 96(8):e63. doi: 10.2106/JBJS.L.01205. Comparison of deformity with respect to the talus in patients with posterior tibial tendon dysfunction and controls using multiplanarweight-bearing imaging or conventional radiography. Haleem AM1, Pavlov H1, Bogner E1, Sofka Cl, Deland JTI, Ellis SJ1.
10—Subtalar joint instability. Mittlmeier T, Wichelhaus A. Eur J Trauma Emerg Surg. 2015 December; 41(6):623-9. doi: 10.1007/s00068-015-0588-7. Epub 2015 Oct. 28. Review.
11—Weight-bearing-line analysis in supramalleolar osteotomy for *varus*-type osteoarthritis of the ankle. Haraguchi N, Ota K, Tsunoda N, Seike K, Kanetake Y, Tsutaya A. J Bone Joint Surg Am. 2015 Feb. 18; 97(4):333-9. doi
12—Does the subtalar joint compensate for ankle malalignment in end-stage ankle arthritis?Wang B, Saltzman C L, Chalayon O, Barg A. Clin Orthop Relat Res. 2015 January; 473(1):318-25. doi: 10.1007/s11999-014-3960-8. Epub 2014 Oct. 15.
13—The Use of MRI in Evaluating Knee Pain in Patients Aged 40 Years and Older. Adelani M A, et al. J Am Acad Orthop Surg. 2016 September; 24(9):653-9 (Demonstrated that weight bearing xrays of the knee were more valuable than MRI in the evaluation of patients older than 40 years with knee pain)
14—The Combination of the Tunnel View and the Weight-Bearing Anteroposterior Radiographs Improve the Detection of Knee Arthritis. Babatunde, O M, et al. Arthritis. 2016:9786924 (Showed that the addition of the weight bearing tunnel view of the knee is valuable in the evaluation of knee arthritis)
15—Comparison of Pelvic Radiographs in Weightbearing and Supine Positions. Fuches-Winkelmann, et al. Clin Orthop Relat Res 2008 April; 466(4) 809-812 (Demonstrated the usefulness of weight bearing xrays in the evaluation of the acetabular roof obliquity and joint space width in the setting of hip dysplasia and osteoarthritis)
16—High Variability of Observed Weight Bearing During Standing Foot and Ankle Radiographs. Miller, et al. Foot Ankle Int 2017; Vol. 38(6).

What is claimed is:

1. A radiography system for taking a weight-bearing radiograph of a limb or a joint, comprising of:
an x-ray radiator; and
a radiographic equipment, which further comprising
i) an electronic cassette for capturing radiography;
ii) one or more weigh scale;
iii) a console; and
iv) an image acquisition controller;
wherein said console is operatively connected with the image acquisition controller, the x-ray radiator, the weigh scale and the electronic cassette, and weight readings measured by the weigh scale during each x-ray is recorded and communicated to the console.

2. The system of claim 1, wherein the system further comprising a triggering mechanism which activates the weigh scale during an x-ray.

3. The system of claim 2, wherein said triggering mechanism is triggered by visual cue or audio cue.

4. The system of claim 1, wherein said weigh scale is incorporated into a radiograph cassette protector or a x-ray stand.

5. A x-ray stand for taking weight-bearing radiograph of a patient, comprising:
a) a platform with a top surface, wherein said top surface further comprising
i) at least one radiolucent plate; and
ii) a radiopaque frame supporting said radiolucent plate;
b) at least one weigh scale that is operatively connected to said radiolucent plate, and affixed to said radiopaque frame.

6. The x-ray stand of claim 5, wherein said x-ray stand is an x-ray stand platform, or a radiograph cassette protector.

7. The x-ray stand of claim 5, wherein said x-ray stand contains at least one cavities directly under said radiolucent plate sized and adapted to receive x-ray cassette.

8. The x-ray stand of claim 5, wherein said weight scale comprising an electric or mechanical weigh measuring mechanism.

9. The x-ray stand of claim 8, wherein said weigh measuring mechanism is housed in the radiopaque frame of said x-ray stand.

10. The x-ray stand of claim 5, wherein said x-ray stand contains one or more receptor slot or holder adapted to support vertical placement of a radiograph cassette adjacent to said radiolucent plate.

11. The stand of claim 5, wherein said weigh scale further comprises a triggering mechanism that activates said weigh scale on visual cue or audio cue.

12. A weight scale board for taking weight-bearing x-ray of the foot, leg, knee or other joint, comprising
a) a base unit, said base unit configured in size and shape to securely and stably hold one or more weight sensing platform, which further comprise a radiolucent plate and a radiopaque housing;
b) at least one anchor point disposed on said base in a vicinity of a terminal end of said weight sensing platform; and
c) a resistance mechanism attached to said anchor point such that when a user positioned on said weight sensing platform and exerts a force on said resistance mechanism, said weight sensing platform senses said exerted force and an apparent shift in a center of balance occasioned by said exerted force during a weight-bearing x-ray.

13. The weight scale board of claim 12, wherein a x-ray cassette receptor is provided directly below each radiolucent plate sized and adapted to receive an x-ray cassette.

14. The weight scale board of claim 12, wherein said weight resistance mechanism, and said anchor point are provided within said radiopaque housing.

15. A method for measuring a weight placed by patient during weight-bearing radiograph using the system of claim 1, comprising
   a) having a patient stand on the stand of claim 1, firmly placing at least one foot on a radiolucent plate;
   b) inserting a radiograph cassette;
   c) taking a radiograph of the patient' foot and ankle; and
   d) measuring weight placed on said radiolucent plate during radiography process.

16. A method for measuring weight placed by a patient during a comparative weight-bearing radiograph using system of claim 1,
   a) positioning a patient on a weigh scale board or stand of this invention against the upright detector with each foot standing in two weigh scale areas;
   b) flexing said patient's knee at approximately 45° with grid in front of knees;
   c) directing x-ray beam approximately 10° caudal from the horizontal plane through the knee joint
   d) activating the x-ray either manually, via audio and/or visual signal or automatically when a preset target weight ratio between the two weigh scale areas is achieved;
   e) measuring weight placed on each foot during radiograph;
   f) recording or displaying or communicating measured weight to the console.

17. A method for taking a weight-bearing X-ray of a patient's knee when the patient takes a slight forward lunge using system of claim 1:
   a. positioning the patient to stand on a weigh scale board face toward a vertical grid device on a upright detector;
   b. asking the patient to take a step forward into a slight lunge, so the patient's two feet are standing in two different weigh scale areas;
   c. ensuring the patient's toes straight ahead, with feet separated enough for good balance, and weight equally distributed on feet;
   d. directing central ray parallel to the joint surface of the tibial plateau;
   e. activating the x-ray either manually, via audio and/or visual signal or automatically when a preset target weight ratio between the two weigh scale areas is achieved;
   f. measuring weight placed on each weigh area scale and/or a total weigh placed on the weigh scale during x-ray.

* * * * *